United States Patent [19]

Girbes Juan et al.

[11] Patent Number: 6,008,324
[45] Date of Patent: *Dec. 28, 1999

[54] NON-TOXIC RIBOSOME INACTIVATING PROTEINS (RIPS) WITH TWO CHAINS, PROCESS FOR THE PREPARATION THEREOF AND APPLICATIONS

[75] Inventors: Tomas Girbes Juan; Jose Miguel Ferreras Rodriguez; Rosario Iglesias Alvarez; Lucia Citores Gonzalez; Francisco Javier Arias Vallejo, all of Valladolid; Ma Angeles Rojo Rodriguez, Palencia; Raquel Munoz Martinez, Soria; Pilar Jimenez Lopez; Fernando Martinez De Benito, both of Valladolid, all of Spain

[73] Assignee: Universidad De Valladolid, Valladolid, Spain

[*] Notice: This patent issued on a continued prosecution application filed under 37 CFR 1.53(d), and is subject to the twenty year patent term provisions of 35 U.S.C. 154(a)(2).

[21] Appl. No.: 08/890,129

[22] Filed: Jul. 9, 1997

Related U.S. Application Data

[63] Continuation of application No. 08/332,595, filed as application No. PCT/ES94/00020, Mar. 2, 1994.

[30] Foreign Application Priority Data

Mar. 2, 1993 [ES] Spain ........................................ 9300408
Mar. 2, 1993 [ES] Spain ........................................ 9300409

[51] Int. Cl.$^6$ ......................... C07K 14/415; A61K 35/78
[52] U.S. Cl. ............................. 530/370; 435/183
[58] Field of Search ............................. 435/183; 530/370

[56] References Cited

U.S. PATENT DOCUMENTS 4,742,046 5/1988 Bliah ............................................ 514/8

OTHER PUBLICATIONS

Biotechnology vol. 10, Apr. 1992 pp. 48 to 49.
Plant Molecular Biology, vol. 22, No. 6, Sep. 1993, "Isolation and Partial Characterization of Nigrin B. A Non–Toxic Novel Type 2 Ribosome–Inactivating Protein From The Bark of *Sambucus nigra L.*" pp. 1181–1186.
Journal of Biological Chemistry, vol. 268, No. 24, Aug. 25, 1993, "Ebulin 1, A Nontoxic Novel Type 2 Ribosome–Inactivating Protein From *Sambucus ebulus L.*Leaves", pp. 18195–18199.

*Primary Examiner*—Chhaya D. Sayala
*Attorney, Agent, or Firm*—Darby & Darby

[57] ABSTRACT

The invention discloses ribosome inactivating proteins (RIPs) with two chains, which are not toxic in the extracellular environment, of plant origin, and capable of interacting with ribonucleic acid and causing the inhibition of the biosynthesis of proteins in cellular systems, said proteins being comprised of two chains A and B, chain A having a N-glucosidase activity of the ribosomal ribonucleic acid, and chain B having a lectine activity, both chains being joined by disulphide bridges. Among the proteins, Nigrine b isolated from bark of *Sambucus nigra L.*, basic Nigrine 1 isolated from the leaves of *Sambucus nigra L.*, Ebuline 1 isolated from leaves of *Sambucus ebulus L.* and Racenosine b isolated from the bark of *Sambucus racemosa L.* are mentioned. The proteins find application as inactivators of the rebonucleic acid and as inhibitors of the protein synthesis.

15 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Sambucus nigra (vii) IMMEDIATE SOURCE:
        (B) CLONE: Nigrin b, Chain A (xi) SEQUENCE DESCRIPTION: SEQ ID NO:1:

```
Ile Asp Tyr Pro Ser Val Ser Phe Asn Leu Asp Gly Ala Val Ser Ala
1               5                   10                  15

Thr Tyr Arg Asp Phe Leu Ser Asn
            20
```

(2) INFORMATION FOR SEQ ID NO:2:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
           (A) ORGANISM: Sambucus nigra (vii) IMMEDIATE SOURCE:
           (B) CLONE: Nigrin b, Chain B (ix) FEATURE:
           (A) NAME/KEY: Peptide
           (B) LOCATION: 1..24
           (D) OTHER INFORMATION: /product= "OTHER"
               /note= "Xaa at position 5 represents any amino acid.  Xaa
                  at position 8 represents any amino acid. Xaa at position
                  22 represents any amino acid."

(xi) SEQUENCE DESCRIPTION: SEQ ID NO:2:

Asp Gly Glu Thr Xaa Thr Leu Xaa Thr Ser Phe Thr Arg Asn Ile Val
1               5                  10                  15

Gly Arg Asp Gly Leu Xaa Val Asp
            20

(2) INFORMATION FOR SEQ ID NO:3:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
          (A) ORGANISM: Sambucus nigra (vii) IMMEDIATE SOURCE:
          (B) CLONE: Base Nigrin 1, Chain B (ix) FEATURE:
          (A) NAME/KEY: Peptide
          (B) LOCATION: 1..8
          (D) OTHER INFORMATION: /product= "OTHER"
              /note= "Xaa at position 3 represents any amino acid. Xaa
                 at position 7 represents any amino acid. Xaa at position
                 8 represents any amino acid."

(xi) SEQUENCE DESCRIPTION: SEQ ID NO:3:

Ala Pro Xaa Tyr Pro Thr Xaa Xaa
1               5

(2) INFORMATION FOR SEQ ID NO:4:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
          (A) ORGANISM: Sambucus ebulus

```
    (vii) IMMEDIATE SOURCE:
          (B) CLONE: Ebulin 1, Chain A (xi) SEQUENCE DESCRIPTION: SEQ ID NO:4:

Ile Asp Tyr Pro Ser Val Ser Phe Asn Leu Ala Gly Ala Lys Ser Thr
1               5                   10                  15

Thr Tyr Arg Asp Phe Leu Lys Asn Leu
            20                  25

(2) INFORMATION FOR SEQ ID NO:5:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
          (A) ORGANISM: Sambucus ebulus (vii) IMMEDIATE SOURCE:
          (B) CLONE: Ebulin 1, Chain B (ix) FEATURE:
          (A) NAME/KEY: Peptide
          (B) LOCATION: 1..25
          (D) OTHER INFORMATION: /product= "OTHER"
              /note= "Xaa at position 5 represents any amino acid. Xaa
              at position 18 represents any amino acid."

(xi) SEQUENCE DESCRIPTION: SEQ ID NO:5:

Asp Gly Glu Thr Xaa Ala Ile Pro Ala Pro Phe Thr Arg Arg Ile Val
1               5                   10                  15

Gly Xaa Asp Gly Leu Glu Val Asp Pro
            20                  25
```

NON-TOXIC RIBOSOME INACTIVATING PROTEINS (RIPS) WITH TWO CHAINS, PROCESS FOR THE PREPARATION THEREOF AND APPLICATIONS

This is a continuation of application Ser. No. 08/332,595, filed Oct. 28, 1994 now abandoned, which is the National Stage filing of PCT/ES94/00020, filed Mar. 2, 1994.

TECHNICAL FIELD OF THE INVENTION

The present invention fits in the technical field of ribosome-inactivating proteins (RIPs) which prevent ribosome functioning catalytically by inactivating ribonucleic acid.

More specifically, the present invention refers to non-toxic novel two-chain RIPs with potential use in cancer therapy and acquired immunodeficiency syndrome (AIDS.)

PRIOR ART OF THE INVENTION

In the plant kingdom there are some species that contain protein biosynthesis inhibitory activity in systems derived from Eukaryotic organisms, which are of a protein type and which awaiting a precise biochemical definition are known as ribosome-inactivating proteins (RIPs) (Gasperi-Campani et al., *Biochem. J.* 186, 439–441 [1980]; Gasperi et al., *J. Nat. Prod.* 48, 446–454 [1985]; Ferreras et al., *Cell. Mol. Biol.* 35, 89–95 [1989]; Merino et al., *J. Exp. Bot.* 41, 67–70 [1990]; Girbes et al., *Cell. Mol. Biol.* 38, 803–812 [1992]; Citores et al., *Cell. Mol. Biol.* 39, 885–995 [1993]; Stirpe et al., *Biotechnology* 10, 405–412 1992; Citores et al., *FEBS Lett.*, 329, 59–62 [1993]. These proteins may have a polypeptide chain (type 1), two polypeptide chains (type 2) or four polypeptide chains (type 4.) (Citores et al., *FEBS Lett.* 329, 59–62 [1993]). The one polypeptide proteins are ribosome ribonucleic acid N-glycosidases (Stirpe et al., *Nuc. Acid Res.* 16, 1349–1357 [1988]), while the two chain proteins have a ribosome ribonucleic acid N-glucosidase (chain A) and a lectin (chain B) (Stirpe et al., *Biotechnology* 10, 405–412 [1993]) which normally recognize galactose residues and derivatives thereof. Four chain proteins are formed by two A–B type dimers (each one equivalent to a type 2 molecule) (Citores et al., *FEBS Lett.*, 329, 59–62 [1993]). These proteins (A and B) have a molecular mass (Mr) between 20000 and 34000. Chains A prevent ribosome functioning catalytically by inactivation of the ribonucleic acid (Jimenez and Vázquez, *Annu. Rev. Microbiol.*, 39 649–672 [1985]; Roberts and Selitrennikoff, *Biosc. Rep.* 6, 19–29 [1986]; Stirpe and Barbieri, *FEBS. Lett.*, 195, 1–8 [1986]; Stirpe et al. Biotechnology 10, 405–412 [1992]; Citores et al., FEBS Lett. 329, 59–62 [1993]; Girbes et al., *J. Biol. Chem.* 268, 18195–18199 [1993]; Girbes et al., *Plant Mol. Biol.* 22, 1181–1186 [1993]. The inactivation consists of freeing an adenine of the larger rRNA of the ribosome (Endo and Tsurugi, *J. Biol. Chem.* 262, 8128–8130 [1987]; Stirpe et al. *Nucleic Acid Res.* 16, 1349–1357 [1988]; Girbes et al., *J. Bacteriol,* 175, 6721–6724; Iglesias et al., *FEBS Lett.,* 325, 291–294 [1993], Iglesias et al., *FEBS. Lett.* 318, 189–192 [1993]). The biological role of these toxins in the plant that produces them is totally unknown (Roberts and Selitrennikoff *Biosc. Rep,* 6, 19–29 [1986]). These proteins are immunologically and chemically different from each other although they have some N-terminal amino-acid sequence homology particularly when the toxins belong to the same botanic family (Montecucchi et al., *Int. J. Peptide Protein Res.* 33, 263–267 [1989]; Arias et al., Planta 186, 532–540 [1992]).

The enormous interest of ribosome-inactivating proteins lies on their use in constructing immunotoxins for cancer therapy (Vitetta and Uhr. *Annu. Rev. Immunol.,* 3, 197–212 [1985]; Frankel et al., *Annu. Rev. Med.* 37, 125–142 [1986]; Koppel, *Bioconj. Chem.* 1, 13–23 [1990]; Lord, Plant Physiol., 85, 1–3 [1987]) and for acquired immunodeficiency syndrome therapy (Till et al., *Science* 242, 1166–1168 [1988]; Ghetie et al., *Bioconj. Chem.,* 1, 24–31 [1990]; Kahn et al., *AIDS* 4, 1197–1204 1993, Byers et al., AIDS 4, 1189–1196 [1992]).

Very recently it has been found that at least four proteins of this family (RIPs) have per se activating nature of HIV-1 RNA virus which is the etiological agent of acquired immunodeficiency syndrome (McGrath et al., *Proc. Natl. Acad. Sci. USA* 86, 2844–2848 [1989]; Lee-Huang et al., *FEBS. Lett.* 272, 12–18 [1990]; Lee-Huang et al., *Proc. Natl. Acad. Sci. USA* 88, 6570–6574 [1991]; Zarling et al., Nature 347, 92–95 [1990]).

The type 2 RIPs and in particular ricin has also displayed antitumorigenic activity (Barbieri and Stirpe, Cancer Surv. 1, 489–520 [1982].)

However, use of toxic one-chain RIPs or toxic two-chain RIPs involves important advantages, such as put forth in the following paragraphs:

Specifically, the two-chain RIPs existing up to the discovery of the present invention of "non-toxic two-chain RIPs" were: ricin, abrin, volkensin, viscumin and modeccin revised in Stirpe et al. *Biotechnology* 10, 405–412 [1992].) The five proteins are extremely toxic therefore their use in constructing immunotoxins and immunoconjugates leads to highly toxic chemical species whose practical therapeutic use is very difficult.

One way to reduce this toxicity is to administer the formed immunotoxin with some of these proteins, generally ricin, together with lactose to thus reduce the unspecific toxicity due to the toxic protein part (for example ricin) in the immunotoxin. The toxicity of the immunotoxin formed with ricin blocked with lactose and an antibody against an antigen of the target cell is due only to the interaction of the antibody part of the immunotoxin with the antigen and subsequent translocation of the immuntoxin into the inside of the cell Spooner and Lord, *Trends in Biotechnology* 8, 189–193 [(1990).]

To eliminate the unspecific toxicity from ricin ricin has been partially activated chemically by directed mutagenesis or simply forming the immunotoxin only with the A chain of the ricin or other toxic RIPs. All these alternatives have as a result the partial loss of activity of ricin or the toxic RIP in question (Blattler et al., *Cancer Cells* 1, 50–55 [(1989)]. The most recent experiments that have been published indicate that the best way to modify ricin is to chemically alter the interaction of the B chain of the ricin using intact A–B ricin molecule with D-galactose (Lambert et al., *Cancer Research* 51, 6236–6242 [(1991).] However, the solution is not good because it noticeably reduces the activity of the chain A upon protein synthesis of the target cell [Lambert et al., Cancer Research 51, 6236–6242 (1991).]

As to one-chain RIPs, most of them, even being less toxic than toxic two-chain RIPs, are relatively toxic at the doses that would be necessary to attain plasmatic concentrations suitable to therapy (Stirpe et al., *Biotechnology* 10, 405–412 [(1992).] Besides, upon being smaller than the two-chain ones they can be more easily trapped by the liver or kidneys by fluid endocytosis. On the other hand the one-chain RIPs are toxic for macrophages Barbarieri and Stirpe, *Cancer Surveys* 1, 490–520 490–520 (1982) and trophoblasts [Chang et al., *Contraception* 19, 175–184 (1979)].

In contrast to the above cited inconveniences, the non-toxic two-chain RIPs of the present invention have the advantage that maintaining their extraordinary protein synthesis inhibitory activity they can't spontaneously enter the cell. In other words, nature has already done with non-toxic two-chain RIPs that which Biochemists and Molecular Biologists try to do with ricin and other toxic two-chain RIPs. Therefore, use thereof in large doses does not present the danger that conjugates with ricin or other toxic two-chain RIPs have. Another additional advantage is that, using immunotoxins formed with nontoxic two-chain RIPs, breaking the bond or bonds that keep the RIP and the antibody together with the subsequent release of non-toxic RIP, no danger is implied in contrast with what would happen if ricin were released.

Given that proteins are powerful antigenic substances, in order to be able to undertake any type of therapy with them it is necessary to have the broadest possible array of said toxins for the purpose of selecting the least immunoreactive one on the one hand and on the other being able to replace the toxin or toxic part of the immunotoxin as neutralizing antibodies develop in the patient.

DETAILED DESCRIPTION OF THE INVENTION

Just as is indicated in the title, the present invention refers to non-toxic novel two-chain ribosome-inactivating proteins (RIPs), to a process for the preparation thereof and uses thereof.

The cited proteins are novel protein type plant toxins which, on the basis of their chemicophysical and biochemical properties, are classified in the type two or two-chain type plant ribosome-inactivating proteins (RIPs) and are characterized in not being toxic upon being injected into Swiss rats weighing 30 g. at a dose of 1.6 mg. per kg. of body weight.

The novelty of the present invention in contrast to the prior art set forth above lies on the use of nontoxic plants to isolate the cited two-chain RIPs, instead of using toxic plants, which led to the obtainment of toxic two-chain RIPs of the type of ricin, abrin, vokensin, viscumin and modeccin cited above.

The non-toxic novel extracellular proteins of the present invention are comprised of two chains, in other words, an A chain with ribosome ribonucleic acid N-glycosidase activity especially with mammalian ribosome 28S ribonucleic acid N-glycosidase activity and a B chain with lectin activity, linked by disulphide bridges; said novel proteins characterized in that linked to a carrier molecule (antibody, hormone or other protein) recognizable by a membrane receptor present in the target cell, they permit the specific and selective action of chain A on said target cells by inactivation of the ribonucleic acid of the ribosomes thereof, substantially avoiding indiscriminate attack of said RIPs on cells not selected by the carrier molecule, precisely due the lack of extracellular toxicity thereof.

The so-defined proteins of the present invention are capable of catalytically interacting with ribonucleic acid and causing the inhibition of protein biosynthesis in acellular systems. Their inhibitory activity is much greater than non-protein antibiotic inhibitors of protein biosynthesis (Pestka, S. (1977) Inhibitors of protein synthesis. In: Molecular Mechanisms of Protein Biosynthesis. Ed. H. Weissbach and S. Pestka. Academic Press, pp. 468–553.)

Additionally, said proteins have ribosomic ribonucleic acid (rRNA) N-glycosidase activity and human red cell agglutinin ability.

The extraordinary power as an inhibitor of protein biosynthesis and their effect on ribonucleic acid, equivalent to that exhibited for example by PAP (pokeweed antiviral protein, Irvin, *Pharmacol. Ter.* 21, 371–387 1983, a protein with anti-HIV-1 activity (Zarling et al., *Nature* 347, 92–95 1990), make these proteins extremely useful.

The most important uses of the non-toxic two-chain RIPs of the invention are: as in vitro inactivators of ribosomes sensitive to toxin, as in vitro mammalian ribosome ribonucleic acid inactivators, as inhibitors of protein biosynthesis in in vitro systems, as inhibitors of protein biosynthesis in cells and tissues coupled to monoclonal antibodies with contrast to specific receptors in said cells and tissues and as antiviral agents against RNA virue, in particular the HIV causing the human acquired immunodeficiency syndrome (AIDS.)

Likewise, from said proteins it is possible to construct conjugates with other chemical species for the purpose of inhibiting protein biosynthesis by in vivo inactivation of ribosomes of Eukaryotic organisms. Along these lines, given that non-toxic two-chain RIPs have a protein synthesis inhibitory activity in acellular systems higher in almost all the tested systems than intact ricin [Girbes et al., *Plant Molecular Biology* 22, 1181–1186 (1993)] and that administered to intact cultured cells or to 30 g. Swiss rats are not toxic, even at concentrations of 1.6 mg. per kg. of body weight [Girbes et al., *Journal of Biological Chemistry* 268, 18195–18199 (1993); Girbes et al., Plant Molecular Biology 22, 1181–1186 (1993)], if adequately transported to the inside of the cell the effectiveness will be greater than that of ricin. Transporting proteins inside the cell is achieved by coupling them to suitable carriers such as antibodies, hormones or other proteins that may be recognized by specific receptors on the cell surface and that may be internalized [Stirpe et al. Biotechnology 10, 405–412 (1992)]; [Barbieri and Stirpe, *Cancer Surveys* 1, 490–520 (1982)].

The non-toxic two-chain RIPs of the present invention can also be used to inhibit functional (in vivo propagation and in intact cells isolated) from ribonucleic acid, in diseases caused or maintained by virus whose genetic content is ribonucleic acid (RNA virus.)

Finally, said proteins, either free or else in conjugate form with other chemical species, may be used to inactivate specific target cells in human beings and experimental animals.

Therefore, the non-toxic two-chain RIPs of the present invention are potentially useful in cancer therapy and AIDS.

The general process to obtain the non-toxic two-chain RIPs of the present invention comprises isolating the same from non-toxic plants including some first operations of extracting the corresponding part from the plant with an aqueous solution of sodium chloride and monosodium phosphate to obtain an extract that (i) is capable of inhibiting protein synthesis and (ii) has human red blood cell agglutinin ability, followed by concentration of the extracts and purification of the same by means of ion-exchange and/or affinity or molecular exclusion chromatography techniques.

Now then, with the general scope of the non-toxic two-chain RIPs of the present invention it is possible to distinguish between two types, that is to say, acid type nontoxic two-chain RIPs and base type non-toxic two-chain RIPs. Therefore, the processes for isolating the same, although they follow the above cited general scheme, the same has certain modifications basically due to said acid or base nature of the molecules.

In accordance with the above, the process to obtain the acid type non-toxic two-chain RIPs of the present invention comprises the following operations:

a) Selecting a plant or part of a non-toxic plant;
b) Obtaining the protein extract of said plant with sodium chloride and monosodium phosphate;
c) selecting the extracts thus obtained that meet the following two requirements:
   (i) capable of inhibiting protein synthesis in rabbit reticulocyte lysates; and
   (ii) red blood cell agglutinin ability;
d) Affinity chromatography of the extracts that meet the two requirements carried out on acid-treated Sepharose 6B and elution with D-galactose or lactose;
e) Molecular exclusion chromatography of the protein peak of the previous step;
f) Obtaining the protein peaks containing lectins and non-toxic two-chain RIPs;
g) Analysis of the inhibition of protein synthesis of each peak;
h) Selecting the peak that inhibits protein synthesis.

The process to obtain the base type two-chain RIPs of the present invention comprises the following operations:
a) Selecting a plant or part of a non-toxic plant;
b) Obtaining the protein extract of said plant with sodium chloride and mono-sodium phosphate;

c) Selecting the extracts thus obtained that meet the following requirements:

(i) capable of inhibiting protein synthesis in rabbit reticulocyte lysates; and (ii) red blood cell agglutinin ability;

d) Ion-exchange chromatography of the base proteins of said extracts on S-Sepharose FF followed by elution with sodium chloride;

e) dialyzing the protein peak obtained in the previous step;

f) 2nd. ion-exchange chromatography of the dialyzed product on CM-Sepharose FF;

g) Selecting the peaks of the previous step that inhibit protein synthesis, followed by concentration of the same with AMICON;

h) Molecular exclusion chromatography of the product of the previous steps on Hi-Load Superdex 75 with FPLC equipment to obtain the base type non-toxic two-chain RIPs.

Of the non-toxic two-chain RIPs of the present invention the ones isolated from plants of the genus Sambucus deserve special mention.

More specifically, among acid type non-toxic two-chain RIPs the following can be cited:

Nigrin b isolated from the bark of *Sambucus nigra L;* and

Ebulin 1 isolated from leaves of *Sambucus ebulus L;* and among the base type non-toxic two-chain RIPs the following are included:

Base Nigrin l isolated from leaves of *Sambucus nigra L;* and

Racemosin b isolated from the bark of *Sambucus racemosa L.*

A more detailed analysis of the nature and properties of each one of these proteins, as well as of the processes to obtain them will be made hereinafter:

Nigrin b

Nigrin b is isolated from the bark of *Sambucus nigra L.* by means of a process that is characterized by the following steps:

a) extracting the bark of *Sambucus nigra L.* previously ground with an aqueous solution of NaCl and $NaPO_4H_2$;

b) filtering the resulting liquid extract through mesh and centrifuging the filtrate, c) applying the supernatant fluid to a chromatography column to subject it to a process of affinity chromatography, washing the column with an extraction buffer.

d) eluting the column washed with the extraction buffer containing D-galactose and collecting the protein fraction.

e) dialyzing and lyophilizing the protein fraction obtained and subjecting it to molecular exclusion chromatography previously dissolved in NaCl $NaH_2PO_4$, yielding the three peak eluate, of which the second one corresponds to Nigrin b.

By means of this process Nigrin b is obtained in a state of final purity of 99% determined by sodium-dodecyl-sulfate polyacrylamide gel electrophoresis (SDS-PAGE.)

The chromatography of step (c) tends to be carried out with Sepharose 6B gel (comprised of a 6% agarose matrix) treated with acid, normally 0.1 N HCl for three hours at about 50° C. and equilibrating with an extraction buffer.

The chromatography of step (e) tends to be carried out with Hi-Load Superdex 75 gel (comprised of agarose and dextrane.)

The relative molecular mass (Mr) of the Nigrin b thus obtained was determined by polyacrylamide gel electrophoresis, being 26,000 for the A chain and 32,000 for the B chain, in the presence of a reducing agent and 58,000 in the absence thereof.

The amino acid sequence of the amino-terminal end of the two polypeptide chains of the Nigrin b was determined as indicated in Arias et al. (Arias et al., *Planta* 186, 532–540 [1992]). The results obtained were:

```
- Chain A:
                                   (SEQ ID NO:1)
Ile Asp Tyr Pro Ser Val Ser Phe Asn Leu
 1               5                   10

Asp Gly Ala Val Ser ALa Thr Tyr Arg Asp
                15                   20

Phe Leu Ser Asn

- Chain B:
                                   (SEQ ID NO:2)
Asp Gly Glu Thr Xxx Thr Leu Xxx Thr
 1

Ser Phe Thr Arg Asn Ile Val Gly Arg
10                  15

Asp Gly Leu Xxx Val Asp
     20

(Xxx: means that it may be any amino acid.)
```

It has been verified that Nigrin b, thus obtained and characterized has each and every one of the above cited properties and uses for the non-toxic two-chain RIPs in general.

Base Nigrin l

Base nigrin l is isolated from the leaves of *Sambucus nigra L.,* by means of a process which is characterized by the following steps:

a) extracting the leaves of *Sambucus nigra L.,* with an aqueous solution of NaCl and $NaPO_4H_2$;

b) filtering the resulting paste through a mesh and centrifuging the previously acidulated filtrate;

c) subjecting the previously acidulated fluid obtained to ion-exchange chromatography, first washing the column with sodium acetate and afterwards with monosodium phosphate;

d) eluting the washed column with a solution of sodium chloride and monosodium phosphate and collecting the protein fraction;

e) dialyzing the protein fraction against monosodium phosphate and subjecting it to ion-exchange chromatography in ion force gradient separating the fractions that contain base Nigrin l;

The relative molecular mass (Mr) of the base Nigrin l thus obtained was determined by polyacrylamide gel electrophoresis, by the Laemmly process obtaining a Mr value of 66,000 in the absence of a reducing agent and of 32,000 for chain A and 34,000 for chain B in the presence of a reducing agent.

The amino acid sequence of the amino-terminal end was determined as indicated in Arias et al. (Arias et al., Planta 196, 532–540 [1992.]) The results obtained were the following:

```
- Chain A:
Amino acid of the blocked amino-terminal end

- Chain B:
Ala Pro Xxx Tyr Pro Thr Xxx Xxx (SEQ ID NO:3)
 1              5
```

It has been verified that base Nigrin l thus obtained and characterized has each and every one of the above cited properties and uses for non-toxic two-chain RIPs in general.

Ebulin 1

Ebulin 1 is isolated from the plant leaves of *Sambucus ebulus L.* by means of a process that is characterized by the following steps:

a) extracting the plant *Sambucus ebulus L.* (leaves) previously ground with an aqueous solution of NaCl and $NaPO_4H_2$;

b) filtering the resulting liquid extract through a mesh and centrifuging the filtrate;

c) applying the supernatant liquid to a chromatographic column to subject it to a process of affinity chromatography, washing the column with an extraction buffer;

d) eluting the column washed with the extraction buffer containing D-galactose and collecting the protein fraction;

e) concentrating the protein fraction and subjecting it to molecular exclusion chromatography equilibrating the column with NaCl and $NaH_2PO_4$ yielding the protein peak eluate of which the last one corresponds to Ebulin 1.

By means of this process Ebulin 1 is obtained in a state of final purity of 99% determined by sodium-dodecyl-sulfate polyacrylamide gel electrophoresis (SDS-PAGE.)

The chromatography of step (c) tends to be carried out with Sepharose 6B gel (comprised of a 6% agarose matrix) treated with acid, normally 0.1N HCl for about 3 hours at about 50° C. and equilibrating with an extraction buffer.

The chromatography of step (e) tends to be carried out with Hi-Load Superdex gel (comprised of agarose and dextrane.)

The relative molecular mass (Mr) of the Ebulin 1 thus obtained was determined by polyacrylamide gel electrophoresis, being 26,000 for chain A and 30,000 for chain B in the presence of a reducing agent and 56,000 in the absence thereof.

The amino acid sequence of the amino-terminal end of said chains is the following:

```
- Chain A:
                                        (SEQ ID NO:4)
Ile Asp Tyr Pro Ser Val Ser Phe Asn Leu Ala
 1              5                   10

Gly Ala Lys Ser Thr Thr Tyr Arg Asp Phe Leu
            15                  20

Lys Asn Leu
        25

- Chain B:
                                        (SEQ ID NO:5)
Asp Gly Glu Thr Xxx Ala Ile Pro Ala Pro Phe
 1              5                   10

Thr Arg Arg Ile Val Gly Xxx Asp Gly Leu Glu
                                20

Val Asp Pro
        25

(Xxx means that it may be any amino acid)
```

It has been verified that the Ebulin 1 thus obtained and characterized has each and every one of the above cited properties and uses for non-toxic two-chain RIPs in general.

Racemosin b

Racemosin b is isolated from the bark of *Sambucus racemosa L.* by means of a process that is characterized by the following steps:

a) extracting the bark of *Sambucus racemosa* with an aqueous solution of NaCl and $NaPO_4H_2$;

b) filtering the resulting paste through mesh and centrifuging the previously acidulated filtrate;

c) subjecting the previously acidulated fluid to ion-exchange chromatography, first washing the column with sodium acetate and afterwards with monosodium phosphate;

d) eluting the column washed with a solution of sodium chloride and monosodium phosphate and collecting the protein fraction;

e) dialyzing the protein fraction against monosodium phosphate and subjecting it to ion-exchange chromatography in ion force gradient, separating the fractions that contain Racemosin b;

f) subjecting the above concentrated fractions to molecular exclusion chromatography in order to obtain Racemosin b.

The relative molecular mass (Mr) of the Racemosin b thus obtained was determined by polyacrylamide gel electrophoresis by the Laemmly process (Nature 227, 680–685) obtaining a Mr value of 58,000 in the absence of a reducing agent and of 27,500 for the A chain and of 29,500 for the B chain in the presence of a reducing agent.

It has been verified that the Racemosin b thus obtained and characterized has each and every one of the above cited properties and uses for non-toxic two-chain RIPs in general.

EMBODIMENTS OF THE INVENTION

The present invention is additionally illustrated by means of the following examples which do not aim to be restrictive of its scope.

EXAMPLE 1

Nigrin b

This example is divided up into eight parts:

a) obtaining nigrin b from the bark of *Sambucus nigra L.*;
b) determining the apparent molecular mass; c) amino-terminal sequence of the polypeptide chains of Nigrin b; d) N-glucosidase activity on RNA; e) inhibition of the protein biosynthesis; f) toxicity in rats; g) red blood cell agglutinin ability; h) immunological relation.

a) Obtaining Nigrin b 15.1 g. of *Sambucus nigra L.* bark were ground with with 121 ml. of 280 mM sodium chloride and 5 mM monosodium phosphate solution (pH 7.5) at 4° C. for 12 hours. The resulting extract was filtered through cheese-cloth to eliminate remaining solids. The liquid extract was centrifuged at 13000 rpm in a JA-14 rotor (Beckman J1 centrifuge) for 45 minutes and the supernatant (120.8 ml) was collected. The supernatant fluid was applied to a chromatography column (9×2.6 cm) charged with acid-treated Sepharose 6B (50 ml of Sepharose 6B treated with 0.1N HCl for 3 hours at 50° C.) equilibrated with extraction buffer. Then the column was washed with extraction buffer until the absorption at 280 nm reached the base line. Then an extraction buffer containing 200 mM D-galactose was applied. The absorption peak (22.5 ml and a protein concentration of 0.243 mg/ml) was collected, dialized against water and finally lyophilized yielding 7.2 mg. of protein. 5.2 mg. of this protein preparation were dissolved in 0.6 ml of 400 mM NaCl and 5 mM of sodium phosphate (pH 7.5) and were applied in two aliquots each one of 0.3 ml. to a Superdex 75 chromatography column. Fractions of 0.5 ml. were collected and three peaks were obtained. The second peak was electrophoretically homogeneous Nigrin b.

b) Determining the apparent molecular mass of Nigrin b

The relative molecular mass (Mr) was determined by polyacrylamide gel electrophoresis (15% acrylamide and 2.7% bis-acrylamide in the presence of sodium-dodecyl-sulfate, SDS-EGPA) by the Laemmly process Nature 227, 680–685.) The Mr values obtained were 26,000 for the A chain and 32,000 for the B chain, in the presence of a reducing agent and 58,000 in the absence thereof.

c) Amino-terminal sequence of the polypeptide chains of Nigrin b

The amino-terminal sequence of the two polypeptide chains of Nigrin b was determined as indicated in Arias et al. (Arias et al., *Planta* 186, 532–540 [1992]). The results obtained were:

```
- Chain A:
                                        (SEQ ID NO:1)
Ile Asp Tyr Pro Ser Val Ser Phe Asn Leu
1               5                   10

Asp Gly Ala Val Ser Ala Thr Tyr Arg Asp
                15                  20

Phe Leu Ser Asn

- Chain B:
                                        (SEQ ID NO:2)
Asp Gly Glu Thr Xxx Thr Leu Xxx Thr
1               5

Ser Phe Thr Arg Asn Ile Val Gly Arg
10              15
```

-continued
```
Asp Gly Leu Xxx Val Asp
            20
```

(Xxx means that it may be any amino acid)

d) N-glucosidase activity on rRNA

The N-glucosidase activity of Nigrin b was determined by release of the rRNA fragment as a result of the action of aniline in an acid medium on rRNA depurinated by Nigrin b. The release of the rRNA fragment was determined by incubating 100 µl of rabbit reticulocyte lysate with Nigrin b as indicated hereinafter. 100 µl of rabbit reticulocyte lysates were incubated with 0.8 µg in a solution containing 2 mM $MgCl_2$. 10 mM dithiothreitol, 50 mM KCl and 20 mM Tris-HCl (pH 7.8) for 15 minutes at 37° C. Afterwards, the rRNA was extracted from these reaction mixtures with a saturated phenol volume of 100 mM Tris-HCl (pH 7.8), in the presence of 10 mM EDTA. The extraction with phenol was carried out twice more and finally the rRNA was precipitated with two ethanol volumes in 300 mm sodium acetate solution (pH 5.2), at −80° C. for 2 hours. Then the rRNA was treated with 1 volume of 2 M aniline (pH 4.5.) The aniline was extracted with diethyl ether (one volume twice.) The rRNA was then precipitated by precipitation with two ethanol volumes and 300 mM of sodium acetate (pH 5.2.) Electrophoretic analysis of the released fragment was done as follows. The rRNA precipitate obtained in the last step was resuspended in water. 3 µg of rRNA in an electrophoresis buffer were placed in each one of the polyacrylamide gel dishes (4.85% acrylamide and 0.150% bis-acrylamide prepared according to Salustio and Stanley (*J. Biol. Chem.* 265, 582–588 [1992]). The electrophoresis was carried out at 15 mA for 100 min. in a minigel system (Mighty Small, Hoefer.) The staining of the gel was done with 0.5 µg/ml ethidiumbromide for 20 min. The visualization was done with a UV lamp transilluminator at 312 nm.

e) Inhibition of the protein biosynthesis

The in vivo protein biosynthesis inhibition studies were conducted using different acellular systems in the standard conditions described in the corresponding bibliographic references. The results of a typical experiment are indicated in Table 1.

TABLE 1

Effect of Nigrin b on protein biosynthesis carried out by different acellular systems

| Acelullar system | $IC_{50}$ (ng/ml) | Bibliographic ref. |
| --- | --- | --- |
| Rabbit reticulocyte lysates | 1.6 | 1 |
| Rat liver | 12.1 | 1 |
| Wheat germ | >100000 | 1 |
| *Vicia sativa* L. germ | >100000 | 2 |
| Rat brain | 2.3 | 1 |
| *Escherichia coli* | >100000 | 3 |

Refs.: Arias et al. Planta 186, 532–540 [1992]; 2. Arias et al. Phytochemistry 30, 3185–3187 [1991]; 3. Girbes et al. Eur. J. Biochem., 67, 257–265 [1976.] $IC_{50}$ indicates the protein concentration that causes 50% inhibition of protein biosynthesis in the standard conditions of each acellular system. The experiments were conducted in the conditions indicated in the bibliographic references.

f) Toxicity in rats

The studies were carried out on Swiss rats weighing about 30 g.

1.6 mg. of nigrin b per kg. of body weight were injected intraperitoneally without causing any death in a 15-day period.

g) Red blood cell agglutinin ability

The red blood cell agglutination studies were done on plates of 96 dishes using an 0.5% red blood cell solution in a final volume of 0.1 ml.

| Total human blood cell agglutination (mg per ml of protein) | | | | |
|---|---|---|---|---|
| | Blood Groups | | | |
| | A | B | AB | O |
| Nigrin b | 0.025 | 0.0125 | 0.0125 | 0.0125 | h) Immunological relation

Polyclonal antibodies obtained by immunizing rabbits for 1.5 months with Nigrin b react with base Nigrin l, Ebulin 1 and Racemosin b, giving an idea of the immunological relation existing between this family of proteins obtained from plants of the genus Sambucus.

EXAMPLE 2

Base Nigrin l

This example is divided up into eight parts: a) obtaining base Nigrin l from the leaves of *Sambucus nigra L.;* b) determining the apparent molecular mass; c) amino-terminal sequence of the polypeptide chains of base Nigrin l; N-glucosidase activity on RNA; e) inhibition of the protein biosynthesis; toxicity in rats; g) red blood cell agglutinin activity; h) immunological relation.

a) Obtaining base Nigrin L.

500 g. of leaves of *Sambucus nigra L.* were extracted in 4 l. of a solution of 140 mM sodium chloride and 5mM monosodium phosphate (pH 7.2) at 4° C. for 12 hours. The resulting paste was filtered through cheese-cloth to eliminate remaining solids. The liquid extract was acidified to a pH of 4 with glacial acetic acid and the solids that appeared were eliminated by centrifugation at 13000 rpm for 45 min. at 0° C. The eluted fluid (approximately 4 l) was subjected to ion-exchange chromatography in S Sepharose Fast Flow (column of 10×5 cm.) The equilibrated column solution was 10 mM sodium acetate (pH 4.5.) The acidified protein fluid was applied to the column. The part not retained by the column was discarded. Then the column was washed with a 10 mM sodium acetate solution (pH 4.5) until the absorbtion at 280 nm was reduced to the minimum. Then the column was washed with 5 mM monosodium phosphate solution (pH 7). The two washings were discarded. Finally, the column was eluted with a 1M sodium chloride and 5 mM monosodium phosphate solution (pH 7.) The eluted protein was dialyzed against 5mM monosodium phosphate (pH 7.) This protein preparation was then subjected to ion-exchange chromatography in ionic force gradient in CM Sepharose Fast Flow (column of 10.5×2.6 cm) preequilibrated with monosodium phosphate (pH 7.) First the protein was fixed and then the ionic gradient consisting of 0.7 l of 5 mM monosodium phosphate solution (pH 7) and 0.7 l of 300 mM of sodium chloride solution was applied. the velocity was adjusted to 7 ml. per min. and fractions of 10.5 ml. were collected. The fractions 15 to 35 that contained base Nigrin l were collected. The fractions were combined and were concentrated with AMICON and YM10 membrane up to a volume of 10 ml. The concentrate was subjected to molecular exclusion chromatography with Hi-Load Superdex 75-FPLC equilibrated with 0.4 M sodium chloride and 5mM monosodium phosphate solution. The chromatography was carried out in the same buffer and the fractions corresponding to base Nigrin l were combined.

b) Determining the apparent molecular mass

The relative molecular mass (Mr) was determined by polyacrylamide gel electrophoresis (15% acrylamide and 2.7% bis-acrylamide in the presence of sodium-dodecyl-sulfate SDS-PAGE). The Mr value obtained was 66000 in the absence of a reducing agent and of 32000 for the A chain and 34000 for the B chain in the presence of a reducing agent.

c) Amino-terminal sequence of the polypeptide chains of base Nigrin l

The amino-terminal sequence of the two polypeptide chains of base Nigrin l was determined as indicated in Arias et al. (Arias et al., Planta 186, 532–540 [1992]). The results obtained were:

Chain A: With the amino acid of the blocked amino-terminal end

- Chain B:

(SEQ ID NO:3)

Ala Pro Xxx Tyr Pro Thr Xxx Xxx
1               5

(Xxx: means that it may be any amino acid)

d) N-glucosidase activity over the rRNA of base Nigrin l

The N-glucosidase activity of the base Nigrin l was determined as the release of the rRNA fragment as a result of the action of aniline in an acid medium over the rRNA depurinated by 1 base Nigrin l. The release of the rRNA fragment was determined by incubating rabbit reticulocyte lysates with base Nigrin l as indicated hereinafter. 100 µl of rabbit reticulocyte lysates were incubated with 0.5 µg of base Nigrin l in a solution containing 2 mM $MgCL_2$, 10 mM dithiothreitol, 50 mM KCl and 20 mM Tris-HCl (pH 7.8) for 15 min. at 37° C. Afterwards the rRNA was extracted from these reaction mixtures with a saturated phenol volume of 100 mM Tris-HCl (pH 7.8), in the presence of 10 mM EDTA. The extraction with phenol was done twice more and finally the rRNA was precipitated with two ethanol volumes in a 300 mM sodium acetate solution (pH 5.2) at –80° for 2 h. Then the rRNA was treated with 1 volume of 2M aniline (pH 4.5). The aniline was extracted with diethyl ether (one volume twice.) The rRNA was then precipitated by precipitation with two ethanol volumes and 300 mM sodium acetate (pH 5.2). The electrophoretic analysis of the released fragment was carried out as follows. The rRNA precipitate obtained in the last step was resuspended in water. 3 µg of rRNA in an electrophoresis buffer were placed in each one of the polyacrylamide gel dishes (4.85% acrylamide and 0.150% of bis-acrylamide prepared according to Salustio and Stanley (J. Biol. Chem. 265, 582–588 [1990].) Electrophoresis was carried out at 15 mA for 100 min. in a minigel system (Mighty Small, Hoefer.) The staining of the gel was done with 0.5 µg/ml ethidium bromide for 20 min. The visualization was done with an U.V. lamp transilluminator at 312 nm.

e) Inhibition of the protein biosynthesis

The in vitro protein biosynthesis inhibition studies were carried out using as an acellular system rabbit reticulocyte lysate in the standard conditions described in (Arias et al. Planta 186, 532–540 [1992]). The results are indicated in Table 2:

TABLE 2

Effect of base Nigrin 1 on protein biosynthesis in acellular system

| Acellular system | IC$_{50}$ (ng/ml) |
|---|---|
| Rabbit reticulocyte lysates | 1.80 |

IC$_{50}$ indicates the protein concentration that causes 50% inhibition of protein biosynthesis.

f) Toxicity in rats

The studies were carried out on Swiss rats weighing approximately 30 g.

1.6 mg. of base Nigrin 1 per kg. of body weight were injected intraperitoneally without causing any death in a 15-day period.

g) Red blood cell agglutinin activity

The red blood cell agglutination studies were done on plates of 96 dishes using an 0.5% red blood cell solution in a final volume of 0.1 ml.

| | Total human red blood cell agglutination (mg per ml. of protein) | | | |
|---|---|---|---|---|
| | Blood Groups | | | |
| | A | B | AB | O |
| Base Nigrin 1 | 0.160 | 0.160 | 0.160 | 0.160 | h) Immunological relation

Polyclonal antibodies obtained by immunizing rabbits for 1.5 months with base Nigrin 1 react with Nigrin b, Ebulin 1 and Racemosin b, giving an idea of the immunological relation existing between this family of proteins obtained from plants of the genus Sambucus.

EXAMPLE 3

Ebulin 1

This example is divided up into eight parts:
a) obtaining Ebulin 1 from leaves of *Sambucus ebulus L.*;
b) determining the apparent molecular mass; c) amino-terminal sequence of the polypeptide chains of Ebulin 1; d) N-glucosidase activity on RNA; e) inhibition of the protein biosynthesis; f) toxicity in rats; g) red blood cell agglutinin activity; h) immunological relation.

a) Obtaining Ebulin 1

100 g. of leaves of *Sambucus ebulus L.* were ground with 1000 ml. of 280 mM sodium chloride and 5 mM monosodium phosphate solution (pH 7.5) at 4° C. for 12 h. The resulting extract was filtered through cheese-cloth to eliminate the remaining solids. The liquid extract was centrifuged at 13000 rpm in JA-14 rotor (Beckman J 21 centrifuge) and the supernatant (990 ml.) was collected. The supernatant fluid was applied to a chromatography column (9.5×5 cm) charged with 190 ml. of acid-treated Sepharose 6B (250 ml. of Sepharose 6B treated with 0.1N HCl for 3 h. at 50° C.) equilibrated with an extraction buffer. Then the column was washed with an extraction buffer until the absorption at 280 nm dropped to the base line. Then an extraction buffer solution containing 200 mM D-galactose was applied. The absorption peak was collected and concentrated to 7.5 ml. with AMICON and YM10 membrane. The concentrated protein solution was then applied to a Hi-Load Superdex 75 column equilibrated with 400 mM NaCl and 5 mM sodium phosphate (pH 7.5.) The eluate yielded protein peaks of some twenty ml. each, the last one being electrophoretically homogeneous Ebulin 1 (the lowest Mr peak.)

b) Determining the apparent molecular mass

The relative molecular mass (Mr) was determined by polyacrylamide gel electrophoresis (15.0% acrylamide and 2.7% bis-acrylamide in the presence of sodium dodecyl sulfate, SDS-EDPA)-by the Laemmly process (Nature 227, 680–685.) The Mr values obtained were 26000 for the A chain and 30000 for the B chain in the presence of a reducing agent and 56000 in the absence thereof.

c) Amino-terminal sequence of the polypeptide chains of Ebulin 1

The amino-terminal sequence of the two polypeptide of Ebulin 1 was determined as indicated in Arias et al. (Arias et al., *Planta* 186, 532–540 [1992]). The results were:

```
- Chain A:
                                             (SEQ ID NO:4)
   Ile Asp Tyr Pro Ser Val Ser Phe Asn Leu Ala
   1               5                   10

Gly Ala Lys Ser Thr Thr Tyr Arg Asp Phe Leu
                   15                  20

Lys Asn Leu
               25

- Chain B:
                                             (SEQ ID NO:5)
   Asp Gly Glu Thr Xxx Ala Ile Pro Ala Pro Phe
   1               5                   10

Thr Arg Arg Ile Val Gly Xxx Asp Gly Leu Glu
                   15                  20

Val Asp Pro
               25
```

(Xxx: means that it can be any amino acid)

d) N-glucosidase activity on rRNA of Ebulin 1

The N-glucosidase activity of Ebulin 1 was determined as the release of the rRNA fragment as a result of the action of aniline in an acid medium on rRNA depurinated by Ebulin 1. The release of the rRNA fragment was determined by incubating 100 μl of rabbit reticulocyte lysates with Ebulin 1 as indicated hereinafter. 100 μl of rabbit reticulocytes lysates were incubated with 6.8 μg of Ebulin 1 in a solution containing 2 mM MgCl$_2$, 10 mM dithiothreitol 50 mM KCl and 20 mM Tris-HCl (pH. 7.8) for 15 min. at 37° C. Then the rRNA was extracted from these reaction mixtures with a saturated phenol volume of 100 mM Tris-HCl (pH 7.8) in the presence of 10 mM EDTA. The phenol extraction was done twice more and finally the rRNA was precipitated with two ethanol volumes in a 300 mM sodium acetate solution (pH 5.2) at −80° C. for 2 h. Then the rRNA was treated with 1 volume of 2 M aniline (pH 4.5). The aniline was extracted with diethyl ether (one volume twice.) The rRNA was then precipitated with two ethanol volumes and 300 mM sodium acetate (pH 5.2). The electrophoretic analysis of the freed fragment was done as follows. The rRNA precipitate obtained in the last step was resuspended in water. 3 μg of rRNA in an electrophoresis buffer were placed in each one of the polyacrylamide gel dishes (4.85% acrylamide and 0.150% bis-acrylamide prepared according to Salustio and Stanley (J. Biol. Chem. 265, 582–588 [1990]). The electrophoresis was carried out at 15 mA for 100 min. in a minigel system (Mighty Small, Hoefer.) The staining of the gel was done with 0.5 μg/ml ethidium bromide for 20 min. The visualization was done with an U.V. lamp transilluminator at 312 nm.

e) Inhibition of the protein biosynthesis

The in vitro protein biosynthesis inhibition studies were carried out using different acellular systems in the standard conditions described in the bibliographic references. The results of a typical experiment are indicated in Table 3.

TABLE 3

Effect of Ebulin 1 on protein biosynthesis carried out by different acellular systems

| Acellular system | $IC_{50}$ (ng/ml) | Bibliographic ref. |
|---|---|---|
| Rabbit reticulocyte lysates | 8.5 | 1 |
| Rat liver | 15 | 1 |
| Wheat germ | >100000 | 1 |
| Vicia sativa L. germ | >100000 | 1 |
| Ratbrain | 5 | 1 |
| Escherichia coli | >100000 | 3 |

Refs.: 1. Arias et al. Planta 186, 532–540 1992: 2. Arias et al. Phytochemistry 30, 3185–3187 1991; 3. Girbes et al. Eur. J. Biochem. 67, 257–265 1976 $IC_{50}$ indicates the protein concentration that causes 50% inhibition of protein biosynthesis in the standard conditions of each acellular system. The experiments were conducted in the conditions indicated in the bibliographic references.

f) Toxicity in rats

The studies were done on Swiss rats weighing about 30 g. 1.6 mg. of Ebulin 1 per kg. of body weight were injected intraperitoneally without causing any death in a 15-day period.

g) Red blood cell agglutination activity

The red blood cell agglutination studies were done on plates of 96 dishes using a 0.5% red blood cell solution in a final volume of 0.1 ml.

| | Total human blood cell agglutination (mg per ml of protein) | | | |
|---|---|---|---|---|
| | Blood Groups | | | |
| | A | B | AB | O |
| Nigrin b | 0.05 | 0.025 | 0.0125 | 0.0125 | h) Immunological relation

Polyclonal antibodies obtained by immunizing rabbits for 1.5 months with Ebulin 1 reacted with Nigrin b, base Nigrin b and Racemosin b, giving an idea of the immunological relation existing among this family of proteins obtained of the genus Sambucus.

EXAMPLE 4

Racemosin b

This Example is divided up into seven parts:
a) obtaining Racemosin b from the bark of Sambucus racemosa L.; b) determining the apparent molecular mass; c) N-glucosidase activity on RNA; d) inhibition of protein biosynthesis; e) toxicity in rats; f) red blood cell agglutin activity; g) immunological relation.

a) Obtaining Racemosin b 250 g. of bark of Sambucus racemosa L were extracted with 2 l. of 140 mM sodium chloride and 5 mM monosodium phosphate solution (pH 7.2) at 4° C. for 12 h. The resulting part was filtered through cheese-cloth to eliminate the remaining solids. The liquid extract was acidified to a pH 4 with glacial acetic acid and the solids that appeared were eliminated by centrifugation at 13000 rpm for 45 min. at 0° C. The eluated fluid (approximately 2 l) was subjected to ion-exchange chromatography in S Sepharose Fast Flow (column of 8.4×5 cm.) The equilibrated column solution was 10 mM sodium acetate (pH 4.5). The acidified protein fluid was applied to the column. The part not retained by the column was discarded. Then the column was washed with a 10 mM sodium acetate solution (pH 4.5) until the absorption at 280 nm was reduced to the minimum. Then the column was washed with a 5 mM monosodium phosphate solution (pH 7.) The two washings were discarded. Finally, the column was eluted with a 1 M sodium chloride and 5 mM monosodium phosphate solution (pH 7.) The eluted protein was dialyzed against 5 mM monosodium phosphate (pH 7.) This protein preparation was then subjected to ion-exchange chromatography in ion force gradient in CM-Sepharose Fast Flow (column of 4.7×2.6 cm) preequilibrated with monosodium phosphate (pH 7.) First the protein was fixed and then the ion gradient consisting of 0.7 l of 5 mM monosodium phosphate solution (pH 7) and 0.7 l of 300 mM of sodium chloride solution. The velocity was adjusted to 7 ml. per min. and fractions of 10.5 ml. were collected. The fractions 4 to 15 that contained Racemosin b were collected. The fractions were combined and concentrated with AMICON and YM10 membrane to a voume of 10 ml. Then the concentrate was subjected to molecular exclusion chromatography with Hi-Load Superdex 75-FPLC equilibrated with 0.4 mM sodium chloride and 5mM monosodium phosphate solution (pH 7.) The chromatography was carried out in the same buffer and the fractions corresponding to pure Racemosin b were combined.

b) Determining the apparent molecular mass

The relative molecular mass (Mr) was determined by polyacrylamide gel electrophoresis (15% acrylamide and 2.7% bis-acrylamide in the presence of sodium-dodecyl-sulfate, SDS-PAGE) by the Laemmly process (Nature 227, 680–685). The Mr value obtained was 58000 in the absence of a reducing agent and 27500 for the A chain and 29500 for the B chain in the presence of a reducing agent.

c) N-glucosidase activity on rRNA of Racemosin b

The N-glucosidase activity of Racemosin b was determined as the release of the rRNA fragment as a result of the action of aniline in an acid medium on the rRNA depurinated by Racemosin b. The release of the rRNA fragment was determined by incubating 100 $\mu$l of rabbit reticulocyte lysates with Racemosin b as indicated hereinafter. 100 $\mu$l of rabbit reticulocyte lysates were incubated with 0.5 $\mu$g of Racemosin b in a solution containing 2 mM $MgCl_2$, 10 mM dithiothreitol, 50 mM KCl and 20 mM Tris-HCl (pH 7.8) for 15 min. at 37g C. Afterwards the rRNA was extracted with these reaction mixtures with a saturated phenol volume of 100 mM Tris-HCl (pH 7.8) in the presence of EDTA. The phenol extraction was done twice more and finally the rRNA was precipitated with two ethanol volumes in a 300 mM sodium acetate solution (pH 5.2) at −80° C. for 2 h. Then the rRNA was treated with 1 volume of 2 M aniline (pH 4.5). The aniline was extracted with diethyl ether (one volume twice.) The rRNA was precipitated afterwards by precipitation with two ethanol volumes and 300 mM sodium acetate (pH 5.2). The electrophoretic analysis of the freed fragment was done as follows. The rRNA precipitate obtained in the last step was resuspended in water. 3 $\mu$g of rRNA in electrophoresis buffer were placed in each one of the polyacrylamide gel dishes (4.85% acrylamide and 0.150% bis-acrylamide prepared according to Salustio and Stanley (J. Biol. Chem. 265, 582–588 [1990]). The electrophoresis was carried out at 15 mA for 100 min. in a minigel system (Mighty Small, Hoefer.) The staining of the gel was done with 0.5 $\mu$g/ml ethidium bromide for 20 min. The visualization was done with an U.V. lamp transilluminator at 312 nm.

d) Inhibition of the protein biosynthesis

The in vitro protein biosynthesis inhibition studies were carried out using as an acellular system rabbit reticulocyte lysate in the standard conditions described in Arias et al., Planta 186, 532–540 [1992.]) The results are indicated in Table 4.

TABLE 4

Effect of Racemosin b on protein biosynthesis in acellular system

| Acellular system | $IC_{50}$ (ng/ml) |
|---|---|
| Rabbit reticulocyte lysates | 0.54 |

$IC_{50}$ indicates the protein concentration that causes a 50% inhibition of protein biosynthesis.

e) Toxicity in rats

The studies were carried out on Swiss rats weighing approximately 30 g.

1.6 mg of Racemosin b per kg. of body weight were injected intraperitoneally without causing any death in a 15-day period.

f) Red blood cell agglutin activity

The red blood cell agglutination studies were done on plates of 96 dishes using 0.5% red blood cell solution in a final volume of 0.1 ml.

| | Total human red blood cell agglutination (mg per ml. of protein) | | | |
|---|---|---|---|---|
| | Blood Groups | | | |
| | A | B | AB | O |
| Racemosin b | 6.8 | 3.4 | 3.4 | 5.4 | g) Immunologic relation

Polyclonal antibodies obtained by immunizing rabbits for 1.5 months against Ebulin 1 and Nigrin b reacted with Racemosin b, giving an idea of the immunological relation existing among the proteins of this family obtained in plants of the genus Sambucus.

We claim:

1. An isolated and purified protein derived from non-toxic plants and capable of interacting with ribosomal ribonucleic acid to inactivate said ribosomal ribonucleic acid and inhibit protein biosynthesis, said protein comprising two different chains, A and B, linked by a disulfide bridge, wherein chain A has N-glucosidase activity of ribosomal ribonucleic acid and chain B has lectin activity.

2. The protein of claim 1, obtainable according to a method comprising the steps of:
   (a) extracting part of the plant containing said protein with aqueous based sodium chloride and monosodium phosphate; and
   (b) concentrating and purifying said extract of step (1) by one or more chromatography techniques including ion-exchange, affinity and molecular exclusion, yielding an electrophoretically homogeneous protein from among other proteins and lectins.

3. The protein of claim 2, wherein said protein is derived from plants of the genus Sambucus.

4. The protein of claim 1, wherein said protein is derived from plants of the genus Sambucus.

5. The protein of claim 1, wherein said protein is derived from the leaves of *Sambucus ebulus L.*

6. The protein according to claim 5, designated Ebulin 1 and characterized in that said Ebulin 1 has a relative molecular mass determined by polyacrylamide gel electrophoresis of 26,000 for chain A and of 30,000 for chain B in the presence of a reducing agent and 56,000 in the absence thereof.

7. The protein according to claim 6, wherein chains A and B have the following amino acid sequences at the amino-terminal end:
   Chain A:
     Ile Asp Tyr Pro Ser Val Ser Phe Asn Leu Ala
     Gly Ala Lys Ser Thr Thr Tyr Arg Asp Phe Leu
     Lys Asn Leu (SEQ ID NO:4)
   Chain B:
     Asp Gly Glu Thr Xxx Ala Ile Pro Ala Pro Phe
     Thr Arg Arg Ile Val Gly Xxx Asp Gly Leu Glu
     Val Asp Pro
   wherein Xxx represents any amino acid (SEQ ID NO:5).

8. A method for in vita inactivation of ribosomes sensitive to toxins, comprising contacting cells containing said ribosomes with the protein of claim 1.

9. A method for in vitro inactivation of mammalian ribosomal ribonucleic acid comprising contacting mammalian cells with the protein of claim 1.

10. A pharmaceutical composition comprised of the protein of claim 1 and a carrier molecule recognized by a membrane receptor present on a target cell.

11. The pharmaceutical composition of claim 10 wherein the carrier molecule is an antibody, hormone or a protein.

12. A purified protein isolated from a non-toxic plant, which protein is capable of interacting with ribosomal ribonucleic acid for inactivating said ribosomal ribonucleic acid and inhibiting protein bio-synthesis, said protein comprising a first chain A and a second chain B, being linked by disulfide bridges, wherein chain A has ribosomal ribonucleic acid N-glucosidase activity, chain B has lectin activity, and said non-toxic plant is of the genus Sambucus.

13. A method of extracting and purifying a protein from non-toxic plants, said non-toxic protein capable of interacting with ribonucleic acid to inhibit protein biosynthesis and comprising two chains, A and B, linked by disulfide bridges, wherein chain A has ribosomal ribonucleic acid N-glucosidase activity and chain B has lectin activity, comprising the steps of:

(a) extracting part of the plant containing said protein with aqueous based sodium chloride and monosodium phosphate to obtain an extract which inhibits protein synthesis and has human red blood cell agglutinin activity; and (b) concentrating and purifying said extract of step (1) by one or more chromatography techniques including ion-exchange, affinity and molecular exclusion, yielding an electrophonetically homogeneous protein from among other proteins and lectins.

14. The method of claim 13, wherein said protein obtained is of an acidic and step (b) of said method comprises:

(i) subjecting said extract obtained in step (a) to an acid-treated affinity chromatography column, eluting with D-galactose or lactose and collecting the protein fraction;

(ii) subjecting said protein fraction of step (i) to molecular exclusion chromatography and collecting the fractions containing lectins and said protein; and (iii) selecting and obtaining said fraction from step (ii) which inhibits protein synthesis.

15. The method according to claim 13, wherein said protein is designated Ebulin 1, wherein extracting step (a) comprises extracting the previously ground bark of *Sambucus ebulus L.* with an aqueous solution of NaCl and $NaPO_4H_2$ to obtain a liquid extract; and wherein step (b) comprises:

(i) filtering the resulting liquid extract through mesh and centrifuging the filtrate;

(ii) applying the supernatant fluid to an equilibrated affinity chromatography column with an extraction buffer and washing the column with an extraction buffer;

(iii) eluting the washed column with an extraction buffer containing D-galactose and collecting the protein fraction;

(iv) concentrating the protein fraction and applying it to another equilibrated molecular exclusion chromatography column with NaCl and $NaH_2PO_4$, the eluate from the column yielding protein peaks; and (v) collecting the last protein peak which contains Ebulin 1.

* * * * *

UNITED STATES PATENT AND TRADEMARK OFFICE
CERTIFICATE OF CORRECTION

PATENT NO.  : 6,008,324
DATED       : December 28, 1999
INVENTOR(S) : Tomas Girbes Juan et al.

It is certified that error appears in the above-identified patent and that said Letters Patent is hereby corrected as shown below:

Claims,
Please add the following claims:

-- 16. The protein of claim 3, wherein said protein is derived from the leaves of *Sambucus rasemosa L.*

17. A protein according to claim 16, designated Rasemosin b and characterized in that said Rasemosin b has a relative molecular mass determined by polyacrylamide gel electrophoresis of 27,500 for a chain A and 29,500 for a chain B in the presence of a reducing agent and 58,000 in the absence thereof.

18. The protein of claim 3, wherein said protein is derived from the leaves of *Sambucus niger L.*

19. The protein according to claim 18, designated Nigrin b and characterized in that said Nigrin b has a relative molecular mass determined polyacrylamide gel electrophoresis of 26,000 for a chain A and 32,000 for a chain B in the presence of a reducing agent and 58,000 in the absence thereof.

20. The protein according to claim 19, wherein chains A and B have the following amino acid sequences at the amino-terminal end:
    Chain A:
        Ile Asp Tyr Pro Ser Val Ser Phe Asn Leu
        Asp Gly Ala Val Ser Ala Thr Tyr Arg Asp
        Phe Leu Ser Asn (SEQ ID NO:1)
    Chain B:
        Asp Gly Glu Thr Xxx Thr Leu Xxx Thr
        Ser Phe Thr Arg Asn Ile Val Gly Arg
        Asp Gly Leu Xxx Val Asp
wherein Xxx represents any amino acid (SEQ ID NO:2).

UNITED STATES PATENT AND TRADEMARK OFFICE
CERTIFICATE OF CORRECTION

PATENT NO. : 6,008,324
DATED : December 28, 1999
INVENTOR(S) : Tomas Girbes Juan et al.

It is certified that error appears in the above-identified patent and that said Letters Patent is hereby corrected as shown below:

21. The protein acording to claim 18, designated base Nigrin 1 and characterized in that said base Nigrin 1 has a relative molecular mass determined by polyacrylamide gel electrophoresis of 32,000 for the A chain and 34,000 for the B chain in the presence of a reducing agent, and 66,000 in the absence thereof.

22. The protein according to claim 21, wherein chain A is blocked at the amino terminus and chain B has the following amino acid sequence at the amino terminal end:
    Ala Pro Xxx Tyr Pro Thr Xxx Xxx, wherein Xxx represents any amino acid (SEQ ID NO:3). --

Signed and Sealed this

Eleventh Day of September, 2001

*Attest:*

NICHOLAS P. GODICI
*Attesting Officer*     Acting Director of the United States Patent and Trademark Office